US011468347B2

(12) United States Patent
Neumann

(10) Patent No.: US 11,468,347 B2
(45) Date of Patent: Oct. 11, 2022

(54) METHODS AND SYSTEMS FOR PHYSIOLOGICALLY INFORMED GESTATIONAL INQUIRIES

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 428 days.

(21) Appl. No.: 16/778,847

(22) Filed: Jan. 31, 2020

(65) Prior Publication Data

US 2021/0241133 A1 Aug. 5, 2021

(51) Int. Cl.
| | | |
|---|---|---|
| *G06N 5/04* | (2006.01) | |
| *G06N 20/00* | (2019.01) | |
| *G16H 30/20* | (2018.01) | |
| *G16H 50/20* | (2018.01) | |

(52) U.S. Cl.
CPC ............ *G06N 5/04* (2013.01); *G06N 20/00* (2019.01); *G16H 30/20* (2018.01); *G16H 50/20* (2018.01)

(58) Field of Classification Search
CPC .......... G06N 5/04; G06N 20/00; G16H 30/20; G16H 50/20
See application file for complete search history.

(56) References Cited

U.S. PATENT DOCUMENTS 10,068,277 B2  9/2018  Jurgenson et al.

2011/0145017 A1  6/2011  Lee
2012/0173336 A1  7/2012  Strumolo
(Continued)

FOREIGN PATENT DOCUMENTS

AU      2015246142      5/2016

OTHER PUBLICATIONS

Robinson, What can I eat in pregnancy? App aims to answer with help from IBM's Watson, Website Article, Dec. 2015 https://www.theguardian.com/sustainable-business/2015/dec/21/what-eat-pregnancy-app-nutrino-IBM-watson-supercomputer.
(Continued)

*Primary Examiner* — Thai Q Tran
*Assistant Examiner* — Jose M Mesa
(74) *Attorney, Agent, or Firm* — Caldwell Intellectual Property Law

(57) ABSTRACT

A system for physiologically informed gestational inquiries. The system includes a computing device configured to calculate a gestational phase, wherein the gestational phase is calculated by receiving a gestational datum, classifying the gestational datum to a gestational phase, and generating a gestational phase label. The computing device is further configured to receive from a remote device a gestational inquiry. The computing device is further configured to classify a gestational inquiry to an inquiry category. The computing device is further configured to select a gestational machine-learning model. The computing device is further configured to generate a gestational machine-learning model wherein the gestational machine-learning model utilizes a user biological extraction as an input and outputs gestational eligibility. The computing device is further configured to determine the gestational eligibility of a gestational inquiry.

20 Claims, 5 Drawing Sheets

(56) References Cited

U.S. PATENT DOCUMENTS

| | | |
|---|---|---|
| 2014/0156295 A1 | 6/2014 | Cooper |
| 2015/0262249 A1 | 9/2015 | Wical |
| 2015/0364057 A1 | 12/2015 | Catani et al. |
| 2016/0242742 A1* | 8/2016 | Gratacós Solsona .. G16H 50/30 |
| 2020/0107771 A1* | 4/2020 | Penders ............... A61B 5/7264 |
| 2021/0398682 A1* | 12/2021 | Liang .................... G16H 10/40 |

OTHER PUBLICATIONS

Garcia et al., Must-Have Apps for a Healthy Pregnancy, Website Article, 2019 https://www.parents.com/fun/entertainment/gadgets/must-have-healthy-pregnancy-apps/.

* cited by examiner

US 11,468,347 B2

METHODS AND SYSTEMS FOR PHYSIOLOGICALLY INFORMED GESTATIONAL INQUIRIES

FIELD OF THE INVENTION

The present invention generally relates to the field of artificial intelligence. In particular, the present invention is directed to methods and systems for physiologically informed gestational inquiries.

BACKGROUND

Incorrect utilization of products and participation in activities during gestation can have lasting effects. Frequently, decisions made during gestation are uninformed or based off of inconsistent prior findings. There remains to be seen, an ability to determine if products and services are compatible for a user and also compatible based on the gestational phase of the user.

SUMMARY OF THE DISCLOSURE

A system for physiologically informed gestational inquiries, the system comprising a computing device. The computing device is configured to calculate a gestational phase wherein calculating the gestational phase further comprises receiving a gestational datum; classifying the gestational datum to a gestational phase; and generating a gestational phase label. The computing device is further configured to receive, from a remote device operated by a user, a gestational inquiry. The computing device is further configured to classify the gestational inquiry to an inquiry category. The computing device is further configured to select a gestational machine-learning model as a function of the inquiry category. The computing device is further configured to generate a gestational machine-learning model, wherein the gestational machine-learning model utilizes the gestational phase label and a user biological extraction as an input and outputs gestational eligibility. The computing device is further configured to determine utilizing the gestational machine-learning model the gestational eligibility of the gestational inquiry.

A method of physiologically informed gestational inquiries, the method comprising calculating by a computing device, a gestational phase wherein calculating the gestational phase further comprises receiving a gestational datum; classifying the gestational datum to a gestational phase; and generating a gestational phase label. The method further comprises receiving by the computing device, from a remote device operated by a user, a gestational inquiry. The method further comprises classifying by the computing device the gestational inquiry to an inquiry category. The method further comprises selecting by the computing device a gestational machine-learning model as a function of the inquiry category. The method further comprises generating by the computing device a gestational machine-learning model, wherein the gestational machine-learning model utilizes the gestational phase label and a user biological extraction as an input and outputs gestational eligibility. The method further comprises determining by the computing device utilizing the gestational machine-learning model the gestational eligibility of the gestational inquiry.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for physiologically informed gestational inquiries. In an embodiment, a computing device generates a classification algorithm to calculate a gestational phase. A computing device receives a gestational inquiry containing a question or inquiry related to any aspect of a user's life. For instance and without limitation, a gestational inquiry may seek to uncover what types of cosmetics are safe to be used during pregnancy including any time during preconception and anytime during the postpartum when a user may be breastfeeding. In yet another non-limiting example, a gestational inquiry may contain a question seeking to determine what types of physical activity a user can perform who is currently pregnant and in the first trimester. Computing device classifies a gestational inquiry to an inquiry category. Computing device selects a gestational machine-learning model that utilizes a user biological extraction as an input and outputs one or more indicators of gestational eligibility. Computing device determines utilizing a gestational machine-learning model the gestational eligibility of a gestational inquiry.

Figure 1:
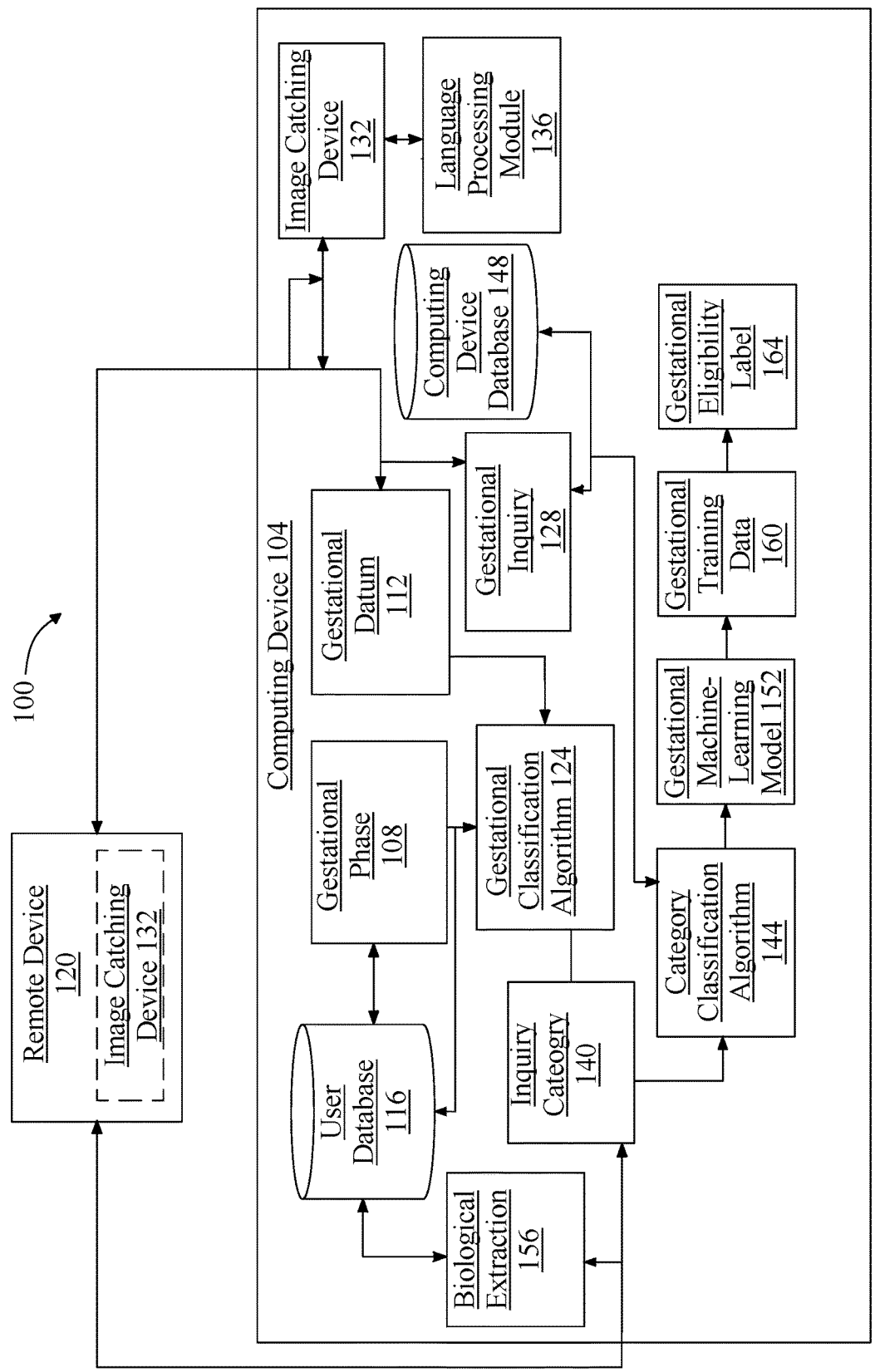
FIG. 1 is a block diagram illustrating an exemplary embodiment of a system for physiologically informed gestational inquiries.

Referring now to FIG. 1, an exemplary embodiment of a system 100 for physiologically informed gestational inquiries is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to calculate a gestational phase 108. A "gestational phase," as used in this disclosure, is any data describing a pregnancy stage. A pregnancy stage may be marked by one or more characteristics of a female as the female carries a developing fetus. A pregnancy stage may include a preconception gestation phase where a female may be considering becoming pregnant but is not currently pregnant. During a preconception gestational phase 108, a female may aim to identify and modify one or more biomedical, behavioral, and/or social risks to the female's health or pregnancy outcome through prevention and management. For example, during a preconception gestational phase 108 a female may start to consume pre-natal vitamins to increase iron stores within her body. In yet another non-limiting example, during a preconception gestational phase 108 a female may gradually reduce and/or eliminate consumption of caffeine. A pregnancy stage may include a conception and implantation phase during which an egg meets up with a sperm cell and fertilization occurs. During a conception and implantation phase a fertilized egg moves to the lining of the uterus and implants to the uterine wall. In an embodiment, a conception and implantation phase may last anywhere from three to seven days. A pregnancy stage may include a first trimester phase which may last from week one through week twelve following conception and implantation. During a first trimester phase a developing embryo and subsequently fetus may begin to develop a heart, lungs, arms, legs, brain, spinal cord and nerves. A pregnancy stage may include a second trimester phase which may last from week thirteen through week twenty seven following conception and implantation. During a second trimester phase a developing embryo may develop eyebrows, eyelashes, fingernails, and neck. In addition, during a second trimester phase a fetus may sleep and wake on regular cycles and the fetus's brain may begin to rapidly develop. A pregnancy stage may include a third trimester phase which may last from week twenty eight to week forty following conception and implantation. During a third trimester phase a fetus may kick and stretch and may respond to light and sound such as music. During a third trimester phase a fetus may have fully mature lungs that are prepared to function on their own. A pregnancy stage may include a postpartum phase which may begin immediately after the birth of a child and last up to two years following the birth of the child. During the postpartum phase a female may nurse her child.

With continued reference to FIG. 1, computing device 104 calculates a gestational phase 108 by receiving a gestational datum 112. A "gestational datum," as used in this disclosure, is any data that is utilized to calculate a gestational phase 108. A gestational datum 112 may describe a user's due date which may be calculated by a medical professional such as a physician and/or nurse. For example, a physician may calculate a user's due date by adding 280 days to the first day of the user's last menstrual period. A gestational datum 112 may describe a user's conception date which may indicate a possible range of days during which a user's baby was conceived whether using artificial or natural methods. For example, a date of conception may reflect a range of days during which sexual intercourse may have led to conception. In yet another non-limiting example, a date of conception may reflect a date of an egg retrieval, a date of an embryo transfer, and/or a date of a blastocyst transfer if a fetus is conceived using artificial methods such as in vitro fertilization. A gestational datum 112 may describe a finding from an ultrasound scan such as a date that a baby's heartbeat is heard or a date when there is first fetal movement. A gestational datum 112 may describe one or more measurements obtained from an ultrasound such as a fundal height measurement or a uterus size measurement.

With continued reference to FIG. 1, one or more gestational datum 112 may be stored within user database 116. User database 116 may be implemented, without limitation, as a relational database, a key-value retrieval datastore such as a NOSQL database, or any other form or structure for use as a datastore that a person skilled in the art would recognize as suitable upon review of the entirety of this disclosure. In an embodiment, one or more gestational datum 112 may be obtained and stored within user database 116 from a remote device 120. Remote device 120 may include without limitation, a display in communication with computing device 104, where a display may include any display as described herein. Remote device 120 may include an additional computing device, such as a mobile device, laptop, desktop, computer and the like. In an embodiment, a remote device 120 may be operated by a medical professional such as a physician or nurse who may record one or more gestational datum 112 during an appointment and/or consultation with a user and transmit them to computing device 104 to be stored within user database 116. A gestational datum 112 may be transmitted to computing device 104 utilizing any network methodology as described herein. In an embodiment, a remote device 120 may be operated by a user who may report to computing device 104 one or more gestational datum 112. For example, a user may enter on remote device 120 the date of her last menstrual period which may be transmitted to computing device 104 to be stored within user database 116.

With continued reference to FIG. 1, computing device 104 is configured to classify a gestational datum 112 to a gestational phase 108. Computing device 104 may classify a gestational datum 112 to a gestational phase 108 by generating a gestational classification algorithm 124. A "gestational classification algorithm," as used in this disclosure is any calculation and/or series of calculations that identify to which set of categories or "bins" a new observation or input belongs. Generating a gestational classification algorithm 124 may include generating a machine learning model using a classification algorithm. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Computing device 104 may utilize a gestational classification model that utilizes a gestational datum 112 as an input and outputs a gestational phase 108.

With continued reference to FIG. 1, computing device 104 is configured to generate a gestational phase label. A "gestational phase label," as used in this disclosure, is any textual, numerical, and/or symbolic data that identifies whether a gestational datum 112 belongs to a particular class or not, where a class may include any gestational phase 108. For example, a gestational phase label may indicate that currently a gestational datum 112 belongs to a second trimester gestational phase label and the gestational datum 112 does not belong to a preconception phase, a conception and implantation phase, a first trimester phase, a third trimester phase, and a postpartum phase.

With continued reference to FIG. 1, computing device 104 is configured to receive, from a remote device 120 operated by a user, a gestational inquiry 128. A "gestational inquiry," as used in this disclosure, is data containing any advice sought and/or question relating to any gestational phase. A gestational inquiry 128 may contain an inquiry related to any gestational phase including advice sought regarding medications including both prescription and non-prescription medications, vitamins, and supplements; pets; household products; fitness; chemicals; food consumption and food recommendations; alcohol consumption and alcohol recommendations; use of cosmetics; building materials such as paint; activities such as sports, leisure time activities; medical treatments; exposure to environmental toxins; travel including travel by cars, planes, trains, boats, and the like. A gestational inquiry 128 may contain advice sought regarding if a user can consume a particular medication while six months pregnant and if so at what dose. In yet another non-limiting example, a gestational inquiry 128 may contain a question regarding if it is safe for a user to have a certain pet live in the user's home throughout user's pregnancy. In yet another non-limiting example, a gestational inquiry 128 may seek advice about what household products are safe to use to clean user's house while pregnant. In yet another non-limiting example, a gestational inquiry 128 may question if a user can consume a particular food or meal while attempting to become pregnant. In yet another non-limiting example a gestational inquiry 128 may seek advice about what types of medical treatments are safe to be performed during a user's third trimester. In yet another non-limiting example, a gestational inquiry 128 may question if a user can use a sauna during the user's pregnancy and if so for how long. In yet another non-limiting example, a gestational inquiry 128 may contain an inquiry regarding any general retail product such as what linens are most suitable for a user or what mattress won't aggravate a user's sciatica problems. Computing device 104 receives a gestational inquiry 128 from a remote device 120 operated by a user. Gestational inquiry 128 may be transmitted from remote device 120 to computing device 104 utilizing any network methodology as described herein.

With continued reference to FIG. 1, computing device 104 is configured to receive at an image catching device 132 located on the computing device 104 a wireless transmission from a remote device 120 containing a picture of the gestational inquiry 128. An "image catching device," as used in this disclosure, is any device capable of taking a picture and/or photograph of any product, item, and/or belonging associated with a gestational inquiry. Image catching device 132 may include a camera, mobile phone camera, scanner or the like. For example, computing device 104 may receive at image catching device 132 a transmission from remote device 120 containing a picture of an over the counter medication such as a topical steroid cream. Computing device 104 may receive at image catching device 132 a wireless transmission from remote device 120 containing a picture of a uniform code commission barcode. For instance and without limitation, user may be shopping at a grocery store and may photograph with an image catching device 132 contained within remote device 120 a photograph of a uniform code commission barcode located on a box of cereal. In an embodiment, image catching device 132 may be contained within remote device 120 and user may take a photograph of a uniform code commission barcode located on an item of clothing using remote device 120. In such an instance, the photograph of the uniform code commission barcode located on the item of clothing may be transmitted to computing device 104 utilizing any network transmission as described herein.

With continued reference to FIG. 1, computing device 104 is configured to receive from a remote device 120 a description of a gestational inquiry. In an embodiment, a description of a gestational inquiry may include a textual narrative describing a gestational inquiry 128. For example, a description of a gestational inquiry may describe that the user is currently experiencing increased back pain while sleeping that keeps the user up at night and the user would like to know what types of exercises will help to alleviate the user's back pain. In such an instance, computing device 104 separates a gestational inquiry 128 from a description of the gestational inquiry whereby the gestational inquiry 128 may be separated to produce "exercise to alleviate back pain." Computing device 104 may separate a gestational inquiry 128 from a description of a gestational inquiry utilizing a language processing module 136. Computing device 104 may separate a gestational inquiry 128 from a description of a gestational inquiry by removing any unnecessary information and/or words that may not be necessary and may contain additional information and/or peripheral details With continued reference to FIG. 1, language processing module 136 may be configured to extract one or more words from a description of a gestational inquiry. Language processing module 136 may include any hardware and/or software module. Language processing module 136 may be configured to extract, from one or more inputs, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

With continued reference to FIG. 1, language processing module 136 may operate to produce a language processing model. Language processing model may include a program automatically generated by a computing device 104 and/or language processing module 136 to produce associations between one or more words extracted from at least a document and detect associations, including without limitation mathematical associations, between such words, and/or associations of extracted words with categories of gestational inquiries. Associations between language elements, where language elements include for purposes herein extracted words describing and/or including questions and/or advice sought relating to any gestational phase 108 may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of gestational inquiries. As a further example, statistical correlations and/or mathematical associations may include probabilistic formulas or relationships indicating a positive and/or negative association between at least an extracted word and/or a given category of gestational inquiry 128; positive or negative indication may include an indication that a given document is or is not indicating a particular category of gestational inquiry 128. For instance, and without limitation, a negative indication may be determined from a phrase such as "symptoms did not indicate greater pain at night," whereas a positive indication may be determined from a phrase such as "symptoms did indicate better pain control with exercise," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory on a computing device 104, or the like.

Still referring to FIG. 1, language processing module 136 and/or a computing device 104 may generate a language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of a gestational inquiry 128. There may be a finite number of categories of gestational inquiries, to which an extracted word may pertain; an HMM inference algorithm, such as the forward-backward algorithm or the Viterbi algorithm, may be used to estimate the most likely discrete state given a word or sequence of words. Language processing module 136 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 136 may use a corpus of documents to generate associations between language elements in a language processing module 136, and a computing device 104 may then use such associations to analyze words extracted from one or more documents and determine that the one or more documents indicate significance of a category of gestational inquiries. In an embodiment, a computing device 104 may perform this analysis using a selected set of significant documents, such as documents identified by one or more experts as representing good science, good clinical analysis, or the like; experts may identify or enter such documents via a graphical user interface as described below, or may communicate identities of significant documents according to any other suitable method of electronic communication, or by providing such identity to other persons who may enter such identifications into a computing device 104. Documents may be entered into a computing device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, a computing device 104 may automatically obtain the document using such an identifier, for instance by submitting a request to a database or compendium of documents such as JSTOR as provided by Ithaka Harbors, Inc. of New York.

With continued reference to FIG. 1, computing device 104 is configured to classify a gestational inquiry 128 to an inquiry category 140. An "inquiry category," as used in this disclosure, is data categorizing a gestational inquiry 128 as having relevance to a particular topic. In an embodiment, an inquiry category 140 may indicate if a gestational inquiry 128 pertains to a medication for example, or if a gestational inquiry 128 pertains to fitness. In an embodiment, an inquiry category 140 may indicate one or more sub-categories that a gestational inquiry 128 may relate to. For instance and without limitation, an inquiry category 140 such as nutrition may be further broken down into sub-categories that include food, supplements, meal plans, individual ingredients, medical foods, absorption, assimilation, food preparation, specific diets, and the like. In yet another non-limiting example, an inquiry category 140 such as general retail may be further broken down into sub-categories that include video, music, electronics, clothing, shoes, jewelry, watches, groceries, games, computers, home, garden, tools, pet supplies, food, beauty, health, toys, kids, baby, handmade, sports, outdoors, automotive, industrial, and the like. An inquiry category 140 may contain information relating to any sub-categories that a gestational inquiry 128 may relate to.

With continued reference to FIG. 1, computing device 104 may classify a gestational inquiry 128 to an inquiry category 140 using a category classification algorithm 144. A "category classification algorithm," as used in this disclosure, is any calculation and/or series of calculations that identify to which set of categories or "bins" a new observation or input belongs. Generating a category classification algorithm 144 may include generating a machine learning model using a classification algorithm. Classification algorithm includes any of the classification algorithms as described above in more detail. In an embodiment, category classification algorithm 144 includes any algorithm suitable for use as gestational classification algorithm 124. Category classification algorithm 144 utilizes a gestational inquiry 128 as an input and outputs an inquiry category 140.

With continued reference to FIG. 1, computing device 104 selects a gestational machine-learning model as a function of an inquiry category 140. In an embodiment, one or more machine-learning models may be previously calculated and loaded into system 100. One or more machine-learning models may be stored in a computing device database 148. Computing device database 148 includes any data structure suitable for use as user database 116. In an embodiment, one or more machine-learning models may be intended for one or more inquiry categories. Computing device 104 may locate a machine-learning model intended for a matching inquiry category 140. For instance and without limitation, computing device 104 may classify a gestational inquiry 128 to an inquiry category 140 such as vitamins. In such an instance, computing device 104 may locate within computing device database 148 a machine-learning model generated for vitamins. In yet another non-limiting example, computing device 104 may classify a gestational inquiry to an inquiry category 140 such as fitness. In such an instance, computing device 104 may locate within computing device database 148 a machine-learning model generated for fitness. In an embodiment, one or more machine-learning algorithms may be organized within computing device database 148 by inquiry category 140 and further organized by one or more sub-categories.

With continued reference to FIG. 1, computing device 104 is configured to generate a gestational machine-learning model 152. A "gestational machine-learning model," as used in this disclosure, is a machine-learning model that utilizes a gestational phase label and a user biological extraction 156 as an input and outputs gestational eligibility labels. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 1, a machine learning process, also referred to as a machine-learning algorithm, is a process that automatedly uses training data and/or a training set as described above to generate an algorithm that will be performed by a computing device 104 and/or module to produce outputs given data provided as inputs; this is in contrast to a non-machine learning software program where the commands to be executed are determined in advance by a user and written in a programming language.

Continuing to refer to FIG. 1, machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

With continued reference to FIG. 1, supervised machine-learning processes may include classification algorithms, defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithms may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

With continued reference to FIG. 1, a "biological extraction 156," as used in this disclosure, contains at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module 136 as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anaerobic bacterial cultures, fecal short chain fatty acids, beta-glucuronidase, cholesterol, chymotrypsin, fecal color, cryptosporidium EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as *Methanobrevibacter smithies*' and *Methanosphaera stadtmanae*. Fungi may include *Candida* species and *Malassezia* species. Viruses may include bacteriophages. *Microbiome* species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, *Anaerotruncus colihominis*, bacteriology, *Bacteroides vulgates*', *Bacteroides-Prevotella*, *Barnesiella* species, *Bifidobacterium longarm*, *Bifidobacterium* species, *Butyrivbrio crossotus*, *Clostridium* species, *Collinsella aerofaciens*, fecal color, fecal consistency, *Coprococcus eutactus*, *Desulfovibrio piger*, *Escherichia coli*, *Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fullness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstenediol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, generating gestational machine-learning model 152 includes receiving gestational training data 160. "Gestational training data," as used in this disclosure, is training data that includes a plurality of gestational phase labels and biological extraction 156 and correlated gestational eligibility. "Training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, computing device 104 outputs a plurality of gestational eligibility labels 164 for gestational inquiries related to an inquiry category 140 utilizing the gestational machine-learning model 152. A "gestational eligibility label," as used in this disclosure, is data containing an indication of either a positive or negative effect on a user's body based on the user's gestational phase 108 and the user's constitution as indicated by the user's biological extraction 156. A positive effect includes a gestational inquiry 128 that will not cause harm to the user and/or the user's fetus. A negative effect includes a gestational inquiry 128 that will cause harm to the user and/or the user's fetus. Computing device 104 may generate a plurality of gestational eligibility labels for gestational inquiries related to an inquiry category 140. For instance and without limitation, a gestational inquiry 128 may contain a question asking if the user can travel to Venezuela, and where the user is currently twenty two months pregnant and currently in the second trimester gestational phase 108. In such an instance, computing device 104 may output a plurality of gestational eligibility label 164 for other areas of travel such as a first gestational eligibility label 164 for travel to Brazil, a second gestational eligibility label 164 for travel to India, a third gestational eligibility label 164 for travel to California, and a fourth gestational eligibility label 164 for travel to Russia.

With continued reference to FIG. 1, computing device 104 is configured to determine utilizing the gestational machine-learning model 152 the gestational eligibility of the gestational inquiry 128. "Gestational eligibility," as used in this disclosure, is data including any textual, numerical, and/or symbolic data indicating whether a gestational inquiry is safe and/or tolerated by a user during one or more gestational phases. In an embodiment, computing device 104 may determine that a gestational inquiry 128 is suitable for a user based on the user's current gestational phase 108. A "suitable" gestational inquiry, as used in this disclosure, is a gestational inquiry that that will have a positive effect on a user. A gestational inquiry 128 may be suitable for a user when a gestational eligibility label indicates that the gestational inquiry 128 will have a positive effect as described above in more detail. A gestational inquiry 128 may not be suitable for a user when a gestational eligibility label 164 indicates that the gestational inquiry 128 will have a negative effect as described above in more detail. Computing device 104 may determine the eligibility of a gestational inquiry 128 for subsequent gestational phase 108 or gestational phase 108 that occur after the current gestational phase 108. A current gestational phase 108 includes any gestational phase 108 that the user is experiencing at the present moment. For instance and without limitation, computing device 104 may determine that a shampoo is suitable for a user who is currently in the first trimester gestational phase 108. In such an instance, computing device 104 may determine the suitability of the same shampoo for the user in the second trimester, the third trimester, and a postpartum phase.

With continued reference to FIG. 1, computing device 104 may determine that a gestational inquiry 128 is suitable for a user and initiate a limitation on a gestational inquiry. A "limitation on a gestational inquiry" as used in this disclosure, is data describing a restriction placed on a gestational inquiry 128. A restriction may indicate a certain maximum number of times a gestational inquiry 128 may be practiced, such as a trip to a tanning salon which may be performed no more than one time per month while the user is breastfeeding and in the postpartum phase. In yet another non-limiting example, a restriction may describe a modification of a gestational inquiry 128. For example, a restriction may indicate that a user who is in the first trimester may engage in physical activity but only if the user's heart rate stays below 100 beats per minute. If the user's heart rate rises above 100 beats per minute, then the user must stop any physical activity that the user is currently engaged in. A restriction may indicate a maximum quantity of a gestational inquiry 128. For example, a restriction may indicate that no more than 4000 mg of acetaminophen may be consumed by the user in any one day during the third trimester.

With continued reference to FIG. 1, computing device 104 may determine that a gestational inquiry 128 is not suitable for a user such as when a gestational eligibility label 164 contains a negative effect. In such an instance, computing device 104 identifies suitable gestational inquiries related to an inquiry category 140. For example, computing 104 may identify gestational eligibility labels generated for gestational inquiries related to the inquiry category 140 that contain a positive effect. Computing device 104 may recommend suitable gestational inquiries related to the inquiry category 140 as a function of the user biological extraction 156 and the user gestational phase 108.

With continued reference to FIG. 1, computing device 104 may determine that a gestational inquiry 128 is not suitable for a first gestational phase 108 where a first gestational phase 108 includes any gestational phase 108 that occurs before a second gestational phase 108. A second gestational phase 108 includes any gestational phase 108 that occurs after a first gestational phase 108. Computing device 104 may determine that the gestational inquiry 128 is suitable for the second gestational phase 108. For instance and without limitation, computing device 104 may determine that hair dye is not suitable for a user in the first trimester or the second trimester but is suitable in the third trimester and in the postpartum phase.

Figure 2:
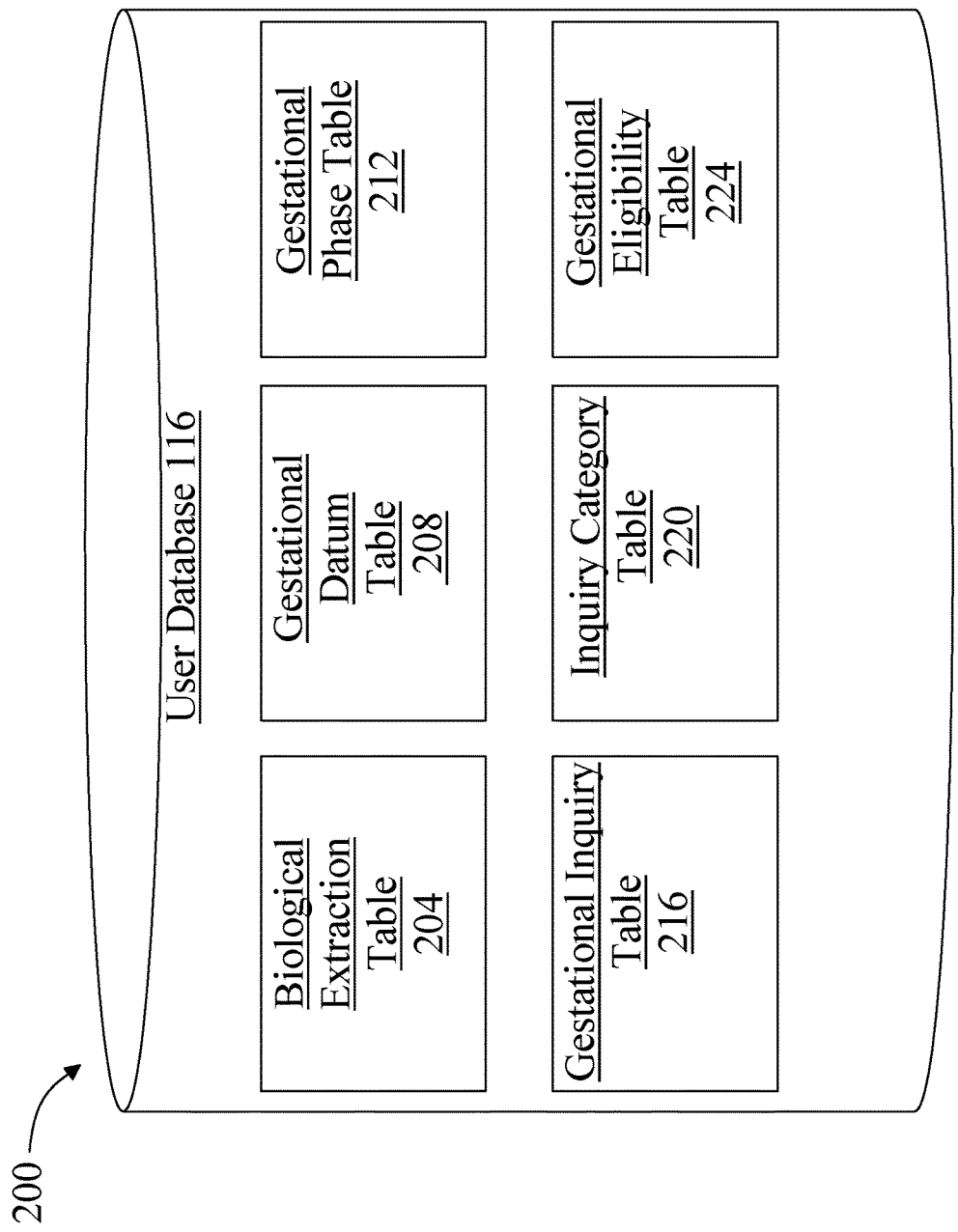
FIG. 2 is a block diagram illustrating an exemplary embodiment of a user database.

Referring now to FIG. 2, an exemplary embodiment of user database 116 is illustrated. User database 116 may be implemented as any data structure as described above in reference to FIG. 1. One or more tables contained within user database 116 may include biological extraction table 204; biological extraction table 204 may include one or more biological extraction 156 pertaining to a user. For instance and without limitation, biological extraction table 204 may include a first entry containing a stool sample analyzed for microbiome strains of bacteria and a second entry containing a blood sample taken from a microchip embedded under a user's skin to measure intracellular and extracellular levels of nutrients including vitamin B1, vitamin C, Vitamin D, Vitamin K, Vitamin E, and Vitamin A. One or more tables contained within user database 116 may include gestational datum table 208; gestational datum table 208 may include one or more gestational datum 112. For instance and without limitation, gestational datum table 208 may include a user's date of conception. One or more tables contained within user database 116 may include gestational phase table 212; gestational phase table 212 may include one or more gestational phase 108 and any corresponding dates and/or documentation. For instance and without limitation, gestational phase table 212 may indicate that a user was in the first trimester until last week when the user entered the second trimester. One or more tables contained within user database 116 may include gestational inquiry table 216; gestational inquiry table 216 may include one or more gestational inquiries generated by a user. For instance and without limitation, gestational inquiry table 216 may contain a gestational inquiry 128 that seeks to determine what type of shampoo a user can safely utilize during her pregnancy. One or more tables contained within user database 116 may include inquiry category table 220; inquiry category table 220 may include information describing one or more inquiry categories that one or more gestational inquiries have been classified to. For instance and without limitation, inquiry category table 220 may include information describing a gestational inquiry 128 pertaining to weightlifting classified to an inquiry category 140 of fitness. One or more tables contained within user database 116 may include gestational eligibility table 224; gestational eligibility table 224 may include one or more gestational eligibility labels. For instance and without limitation, gestational eligibility table 224 may include a gestational eligibility label 164 that indicates that a bamboo mattress will have a negative effect on the user.

Figure 3:
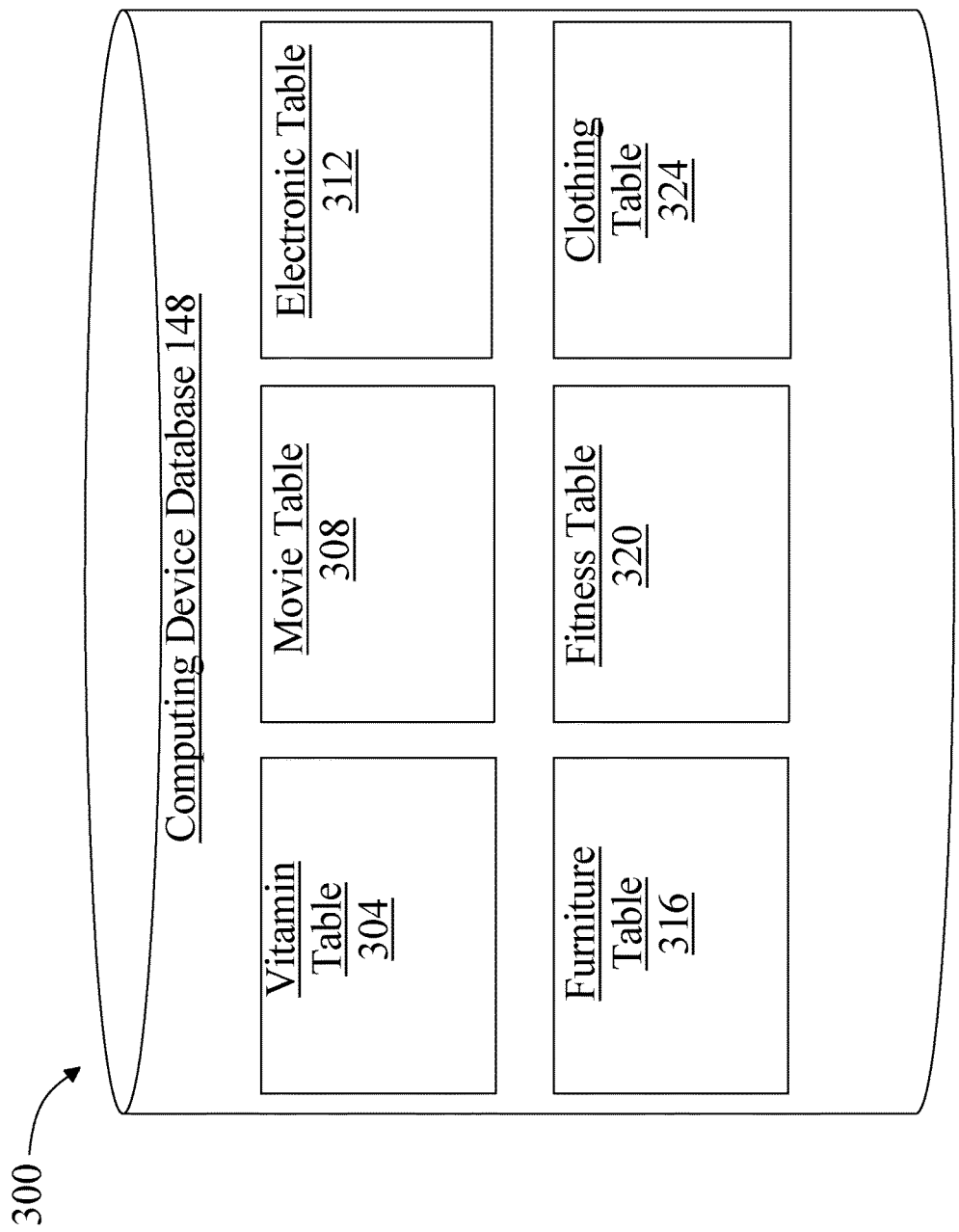
FIG. 3 is a block diagram illustrating an exemplary embodiment of a computing device database.

Referring now to FIG. 3, an exemplary embodiment of computing device database 148 is illustrated. Computing device database 148 may be implemented as any data structure as described above in reference to FIG. 1. One or more tables contained within computing device database 148 may include vitamin table 304. Vitamin table 304 may include one or more machine-learning models created for gestational inquiries classified to an inquiry category 140 of vitamin. One or more tables contained within computing device database 148 may include movie table 308; movie table 308 may include one or more machine-learning models created for gestational inquiries classified to an inquiry category 140 of movie. One or more tables contained within computing device database 148 may include electronic table 312; electronic table 312 may include one or more machine-learning models created for gestational inquiries classified to an inquiry category 140 of electronics. One or more tables contained within computing device database 148 may include furniture table 316; furniture table 316 may include one or more machine-learning models created for gestational inquiries classified to an inquiry category 140 of furniture. One or more tables contained within computing device database 148 may include fitness table 320; fitness table 320 may include one or more machine-learning models created for gestational inquiries classified to an inquiry category 140 of fitness. One or more tables contained within computing device database 148 may include clothing table 324; clothing table 324 may include one or more machine-learning models created for gestational inquiries classified to an inquiry category of clothing.

Figure 4:
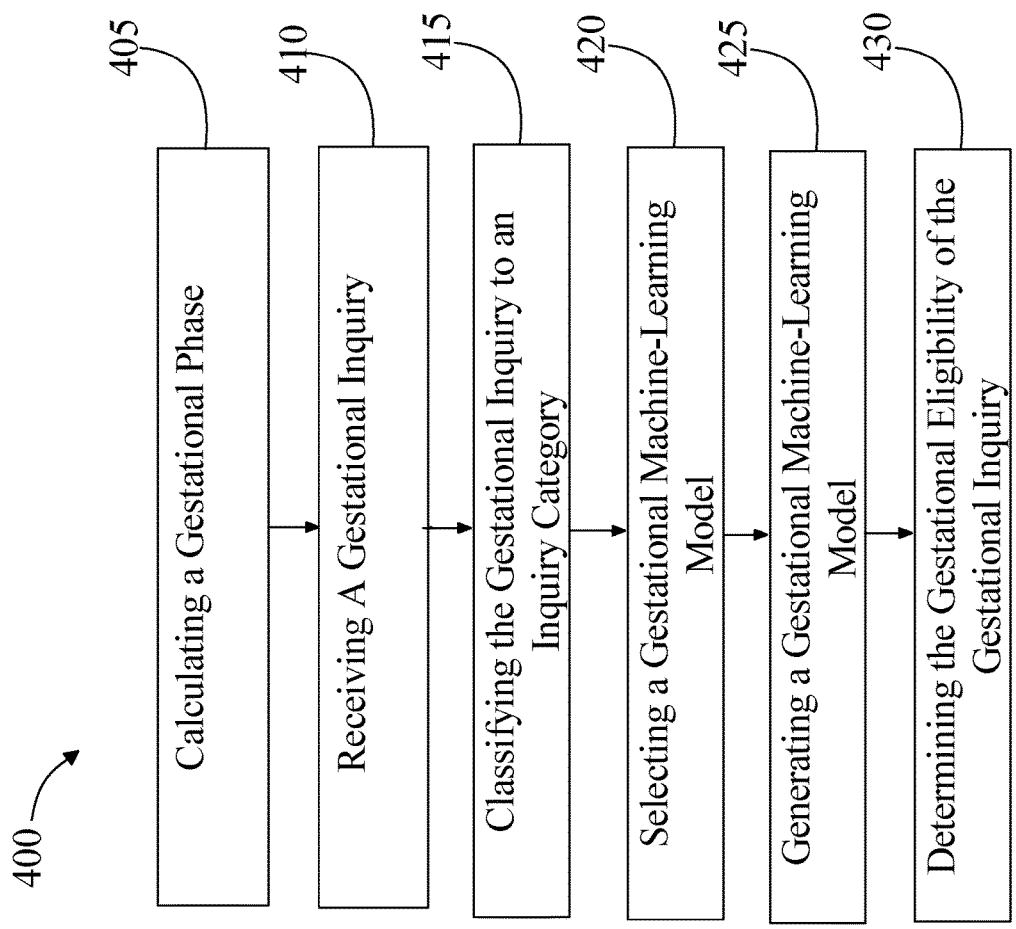
FIG. 4 is a process flow diagram illustrating an exemplary embodiment of a method of physiologically informed gestational inquiries.

Referring now to FIG. 4, an exemplary embodiment of a method 400 of physiologically informed gestational inquiries is illustrated. At step 405, a computing device 104 calculates a gestational phase 108. A gestational phase includes any data describing a pregnancy stage, as described above in more detail in reference to FIG. 1. A pregnancy stage may indicate how far along and/or where in the pregnancy process a particular user is currently at. For instance and without limitation, a pregnancy stage may indicate that a user is in a preconception stage and is merely thinking about the possibility of becoming pregnant. In yet another non-limiting example, a pregnancy stage may indicate that a user is in a postpartum pregnancy stage and is currently three weeks post-delivery and breastfeeding. In yet another non-limiting example, a pregnancy stage may indicate that a user is in a first trimester stage and is currently seven weeks from conception.

With continued reference to FIG. 4, computing device 104 may calculate a gestational phase 108 utilizing a gestational datum 112. A gestational datum 112, includes any data that is utilized to calculate a gestational phase 108 as described above in more detail in reference to FIG. 1. For example, a gestational datum 112 may include a user's expected due date as calculated by a medical professional such as a user's physician. A gestational datum 112 may include an observation from an ultrasound such as how far along developed a fetus appears. One or more gestational datum 112 may be stored in user database 116 as described above in reference to FIGS. 1 and 2. Computing device 104 may receive a gestational datum 112 from a remote device 120. In an embodiment, a remote device 120 such as a mobile phone may be operated by a user who may transmit a gestational datum 112 that describes the date of the user's last menstrual period. In yet another non-limiting example, a remote device 120 such as a computer may be operated by a medical professional who may transmit a gestational datum 112 that contains an observation from a recent ultrasound. Computing device 104 may receive a gestational datum 112 from a remote device 120 utilizing any network methodology as described herein.

With continued reference to FIG. 4, computing device 104 classifies a gestational datum 112 to a gestational phase 108. Classification may be performed by generating a gestational classification algorithm 124. Gestational classification algorithm 124 includes any of the classification algorithms as described above in reference to FIG. 1. For instance and without limitation, gestational classification algorithm 124 may include logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Generating a gestational classification algorithm 124 may include generating one or more machine-learning models. Machine-learning models include any of the machine-learning models as described above in reference to FIGS. 1-3. In an embodiment, one or more machine-learning models may be stored in computing device database 148 as described above in more detail. Gestational classification algorithm 124 utilizes a gestational datum 112 as an input and outputs a gestation phase label. Gestational phase label includes any of the gestational phase labels as described above in reference to FIGS. 1-3. In an embodiment, a gestational phase label may include data that describes a user as currently being in the eighteenth week of pregnancy. In yet another non-limiting example, a gestational phase label may describe a user who is in the postpartum gestational phase and who delivered a baby three weeks prior. In an embodiment, a gestational phase label may indicate and describe how many fetuses are developing inside a user and/or how many babies were delivered. For instance and without limitation, a gestational phase label may indicate that a user is currently pregnant with twins and is currently in her second trimester of pregnancy. In yet another non-limiting example, a gestational phase label may indicate that a user is in the postpartum phase having delivered triplets the previous day. In an embodiment, a gestational phase label may indicate the sex of a fetus and/or the sex of a delivered baby. For instance and without limitation, a gestational phase label may indicate that a user is in the thirty fourth week of the third trimester and is currently pregnant with a female fetus. Computing device 104 generates a gestational phase label containing a description of the gestational phase 108 and any other information described herein utilizing any methodology as described herein.

With continued reference to FIG. 4, at step 410, computing device 104 receives from a remote device 120 operated by a user a gestational inquiry 128. A gestational inquiry, as used in this disclosure, contains a description of any advice sought and/or question relating to any area of a user's life. For instance and without limitation, a gestational inquiry 128 may seek to know what body lotion will be compatible for the user's body while also being safe for the fetus. In yet another non-limiting example, a gestational inquiry 128 may seek to know what seafood is safe to consume while the user is actively trying to become pregnant. In yet another non-limiting example, a gestational inquiry 128 may seek to understand what vaccinations are safe to receive during pregnancy. In yet another non-limiting example, a gestational inquiry may seek to discover what over the counter medication the user should take for an upset stomach while the user is nursing her daughter. In yet another non-limiting example, a gestational inquiry 128 make seek to know what medical procedure the user should have performed while three weeks pregnant for a slipped disc. In yet another non-limiting example, a gestational inquiry 128 may seek to question what type of paint the user should paint user's bedroom while the user is seeking to become pregnant. In yet another non-limiting example, a gestational inquiry 128 may seek to know what recreational activities the user can engage in such as skiing, weightlifting, and/or water sports. In yet another non-limiting example, a gestational inquiry 128 may seek to know what cleaning products the user can use to clean the user's house. In yet another non-limiting example, a gestational inquiry 128 may seek to discover how much caffeine a user can consume and tolerate while pregnant if at all. In yet another non-limiting example, a gestational inquiry 128 may seek to know what types of exercise a user can engage while the user is actively trying to become pregnant. In yet another non-limiting example, a gestational inquiry 128 may seek to understand what prescription medication a user can take while six months pregnant when the user experiences a migraine headache.

With continued reference to FIG. 1, computing device 104 may receive an image of a gestational inquiry 128. Computing device 104 may contain an image catching device 132 that may receive a wireless transmission from a remote device 120 that contains a picture of a gestational inquiry 128. For instance and without limitation, a user may take a picture or photograph of a pillow that a user purchased to determine if the pillow is safe for the user to sleep on each night. In yet another non-limiting example, a user may take a picture of a uniform code commission barcode located on an electronic device to determine the compatibility of the electronic device for the user. In an embodiment, image catching device 132 may be located on remote device 120. For example, a remote device 120 such as a mobile phone may contain a camera or scanner that may allow a user to obtain a picture and/or photograph of a gestational inquiry 128. In an embodiment, a user may browse an online marketplace and may transmit to an image catching device 132 located on computing device 104 a photograph of a product available for sale online such as a kitchen utensil composed of plastic.

With continued reference to FIG. 1, computing device 104 may receive a gestational inquiry 128 that contains a description of a gestational inquiry. A description may contain a textual narrative describing a gestational inquiry 128. For instance and without limitation, a description may contain a textual narrative that describes a series of symptoms that a user has been experiencing, including a burning feeling in the chest behind the breastbone that occurs after eating and that lasts for several hours, chest pain after bending over, burning in the throat, and a hot sour tasting fluid at the back of the throat. In such an instance, the description may also contain a question asking what over the counter medication the user can consume that will alleviate the user's symptoms. Computing device 104 separates a gestational inquiry 128 from a description of a gestational inquiry. In the above referenced example, computing device 104 may separate the description to generate a gestational inquiry 128 that indicates a question regarding an over the counter medication that can alleviate symptoms of burning and chest pain. Computing device 104 may separate a description to generate a gestational inquiry 128 utilizing language processing module 136. This may be performed utilizing any of the methodologies as described above in reference to FIG. 1. In yet another non-limiting example, computing device 104 may receive a gestational inquiry 128 that contains a description that includes details containing a description of twenty five different brands of shampoo with a question that indicates a willingness to know what brand of shampoo is best suited for the user who is seven weeks pregnant. In such an instance, computing device 104 may separate the description regarding the twenty five different brands of shampoo to create a gestational inquiry 128 that contains a desire to know what shampoo is most compatible for a user who is seven weeks pregnant.

With continued reference to FIG. 4, at step 415, computing device 104 classifies a gestational inquiry 128 to an inquiry category 140. Classification may be performed utilizing any of the classification algorithms as described above in reference to FIG. 1. Classification may include generating a category classification algorithm 144. Category classification algorithm 144 includes any of the classification algorithms as described above in reference to FIG. 1. In an embodiment, category classification algorithm 144 utilizes a gestational inquiry 128 as an input and outputs an inquiry category 140. Inquiry category 140 includes any data that categorizes a gestational inquiry 128 as having relevance to a particular topic as described above in reference to FIG. 1. Inquiry category 140 may indicate what aspect or area of a user's life that a gestational inquiry relates to. For instance and without limitation, an inquiry category 140 may indicate that a gestational inquiry that contains advice about the best mascara to utilize may relate to an inquiry category 140 of cosmetics. In yet another non-limiting example, an inquiry category 140 may indicate that a gestational inquiry 128 that contains a question about what types of meats to consume while pregnant may relate to an inquiry category 140 of nutrition. In an embodiment, an inquiry category 140 may contain one or more sub-categories that contain a further delineation of an inquiry category 140 into subsequent, more refined inquiry categories. For instance and without limitation, a gestational inquiry 128 may contain advice about what fabric sweater the user should wear. In such an instance, computing device 104 may classify the previously described gestational inquiry 128 to an inquiry category 140 of clothing and further assign it to a sub-category that includes women's tops.

With continued reference to FIG. 4, at step 420, computing device 104 selects a gestational machine-learning model 152 as a function of an inquiry category 140. Gestational machine-learning model 152 includes any of the machine-learning models as described above in reference to FIG. 1. In an embodiment, computing device 104 may select one or more gestational machine-learning model 152 from computing device database 148. In an embodiment, computing device 104 may match an inquiry category 140 to a machine-learning model intended for the inquiry category 140. This may be performed utilizing language processing module 136. For instance and without limitation, an inquiry category 140 may be generated for electronics which computing device 104 may match to a machine-learning model intended for electronics stored within computing device database 148. In an embodiment, one or more machine-learning models may be organized within computing device database 148 based on the inquiry category 140 that the machine-learning model relates to. For instance and without limitation, an inquiry category 140 may be generated for indoor house plants, which computing device 104 may match to a machine-learning model intended for indoor house plants.

With continued reference to FIG. 4, at step 425, computing device 104 generates a gestational machine-learning model 152. Gestational machine-learning model 152 utilizes a gestational phase label and a user biological extraction 156 as an input and outputs gestational eligibility. Gestational eligibility includes an indication of either a positive or negative effect on a user's body based on the user's gestational phase 108 and the user's constitution as indicated by the user's biological extraction 156. Gestational eligibility may indicate if a particular product or activity included in a gestational inquiry 128 is compatible with a user's biological extraction 156 and a user's gestational phase 108. For instance and without limitation, gestational eligibility may indicate that a deep hair condition that contains methylparaben is compatible for the user's biological extraction 156 which shows the user does not have a methylenetetrahydrofolate reductase mutation (MTHFR) indicating that the user is able to excrete methylparaben and not store methylparaben within the user's body. In such an instance, gestational eligibility may indicate that while the methylparaben is compatible with the user's biological extraction 156, methylparaben is not compatible with the user's gestational phase 108 because the user is in the first trimester and methylparaben may cause birth defects within the first trimester. In such an instance, gestational eligibility may indicate that overall, methylparaben will have a negative effect on the user's body. In yet another non-limiting example, gestational eligibility may indicate that an activity such as riding in a hot air balloon will have a positive effect on a user's body because riding in a hot air balloon is compatible with the user's biological extraction 156, and is safe to engage in when based on the user's current gestational phase 108.

With continued reference to FIG. 4, computing device 104 may generate gestational machine-learning model 152 utilizing gestational training data 160. Gestational training data 160 includes any of the training data as described above in reference to FIG. 1. Gestational training data 160 includes a plurality of gestational phase labels and biological extraction 156 correlated to gestational eligibility. In an embodiment, gestational training data 160 may be stored within computing device database 148. Computing device 104 may output utilizing gestational machine-learning model a plurality of gestational eligibility labels for gestational inquiries related to an inquiry category 140. Gestational eligibility label includes any data that describes gestational eligibility. In an embodiment, computing device 104 may generate a plurality of gestational eligibility labels related to an inquiry category 140. For instance and without limitation, computing device 104 may generate a plurality of gestational eligibility label 164 related to twenty five different types of shampoo for a gestational inquiry 128 related to shampoo and classified to an inquiry category 140 of cosmetics. In yet another non-limiting example, computing device 104 may generate a plurality gestational eligibility label 164 related to all different types of exercise for a gestational inquiry related to exercise and classified to an inquiry category 140 of fitness.

With continued reference to FIG. 4, at step 430, computing device 104 determines utilizing a gestational machine-learning model 152 the gestational eligibility of a gestational inquiry. In an embodiment, determining the gestational eligibility of a gestational inquiry 128 may include evaluating the positive and/or negative effect of a gestational inquiry 128 on a user's biological extraction 156 and the user's gestational phase 108. Computing device 104 may determine that a gestational inquiry 128 is suitable for a user based on the user's current gestational phase 108. In such an instance, computing device 104 evaluates a gestational inquiry 128 to determine eligibility for subsequent gestational phase 108. For instance and without limitation, computing device 104 may determine that a gestational inquiry 128 for an activity such as skiing is suitable for a user in the preconception phase, conception and implantation phase, and the first trimester phase, but not in the second trimester phase, third trimester phase, and the postpartum phase. In yet another non-limiting example, computing device 104 may determine that a gestational inquiry for a particular brand protein bar may be suitable for all gestational phase 108 include preconception, conception and implantation, first trimester, second trimester, third trimester, a postpartum phase. Computing device 104 may determine that a gestational inquiry 128 is suitable for a user and initiate a limitation on a gestational inquiry. A limitation may include any restriction placed on a gestational inquiry 128 as described above in reference to FIG. 1. For instance and without limitation, a limitation may specify that a user can take a cough medicine during the third trimester, but the user cannot use more than two doses per day. In yet another non-limiting example, a limitation may specify that a user can participate in a spinning class at a gym, but the user cannot have a heart rate above 120 beats per minute, otherwise the user must slow down. In yet another non-limiting example, a limitation may specify that a user can use a certain deodorant as much as the user wants during the preconception phase and conception and implantation phase, but the user can only use the deodorant no more than three times each week during the first trimester phase, the second trimester phase, the third trimester phase, and the user cannot use the deodorant at all during the postpartum phase.

With continued reference to FIG. 4, computing device 104 may determine that a gestational inquiry is not suitable for a user and as such may identify suitable gestational inquiries related to an inquiry category 140. For instance and without limitation, computing device 104 may determine that a snake plant is not suitable for a user, where a snake plant may relate to a gestational inquiry 128 classified to an inquiry category 140 of indoor houseplants. In such an instance, computing device 104 identify suitable indoor houseplants which may include for example, bromeliads, jade, pothos, rabbit's ear, and rubber plant. In such an instance, computing device 104 may recommend suitable gestational inquiries related to an inquiry category 140 based on a user's biological extraction 156 and a user gestational phase 108. In the above described example, computing device 104 may identify suitable indoor houseplants by ensuring that the identified suitable indoor houseplants are suitable for the user's biological extraction 156 and the user's gestational phase 108. Computing device 104 may determine that a gestational inquiry 128 is not suitable for a first gestational phase 108 but the gestational inquiry 128 is suitable for a second gestational phase 108 where the second gestational phase 108 occurs after the first gestational phase 108. For instance and without limitation, computing device 104 may determine that hair dye is not suitable in the conception and implantation phase and the first trimester phase, but hair dye is suitable in the second trimester phase, the third trimester phase, and the postpartum phase. In yet another non-limiting example, computing device 104 may determine that mahi mahi is not suitable in the first trimester phase and the second trimester phase but mahi mahi is suitable in the third trimester phase and in the postpartum phase.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
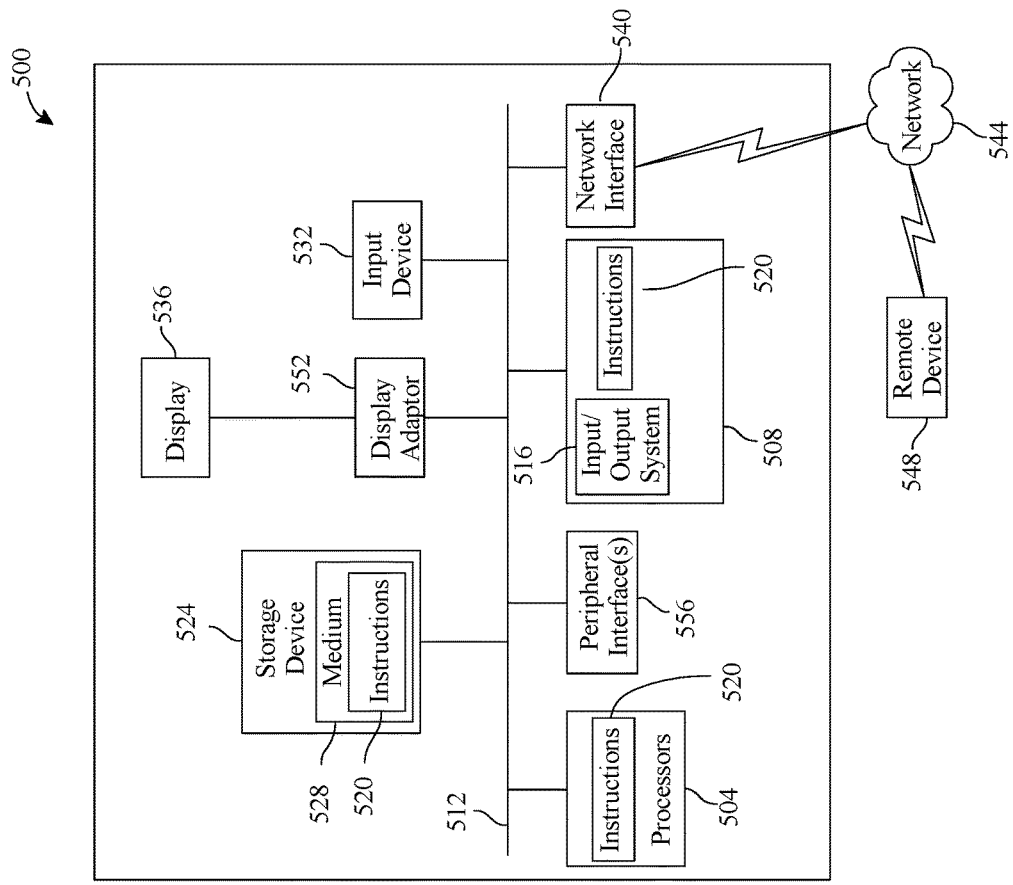
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine-readable media) including, but not limited to, a random access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote device 120 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for physiologically informed gestational inquiries, the system comprising a computing device the computing device designed and configured to:
   calculate a gestational phase, wherein calculating the gestational phase further comprises:
   receiving a gestational datum;
   classifying the gestational datum to a gestational phase; and
   generating a gestational phase label as a function of the classifying;
   receive, from a remote device operated by a user, a gestational inquiry;
   classify the gestational inquiry to an inquiry category;
   select a gestational machine-learning model as a function of the inquiry category;
   generate a gestational machine-learning model, wherein the gestational machine-learning model utilizes the gestational phase label and a user biological extraction as an input and outputs gestational eligibility labels; and
   determine, utilizing the gestational machine-learning model, the gestational eligibility of the gestational inquiry.

2. The system of claim 1, wherein classifying the gestational datum to a gestational phase further comprises generating a gestational classification algorithm, wherein the gestational classification algorithm utilizes the gestational datum as an input and outputs a gestational phase label.

3. The system of claim 1, wherein receiving the gestational inquiry further comprises receiving, at an image catching device located on the computing device, a wireless transmission from the remote device containing a picture of the gestational inquiry.

4. The system of claim 1, wherein receiving the gestational inquiry further comprises:
   receiving from the remote device a description of the gestational inquiry; and
   separating the gestational inquiry from the description of the gestational inquiry.

5. The system of claim 1, wherein classifying the gestational inquiry to an inquiry category further comprises generating a category classification algorithm, wherein the category classification algorithm utilizes the gestational inquiry as an input and outputs an inquiry category.

6. The system of claim 1, wherein generating the gestational machine-learning model further comprises:
   receiving gestational training data, wherein the gestational training data further comprises a plurality of combinations of gestational phase labels and biological extractions correlated to gestational eligibility labels; and
   outputting a plurality of gestational eligibility labels for gestational inquiries related to the inquiry category.

7. The system of claim 1, wherein determining the gestational eligibility of the gestational inquiry further comprises:
   determining that the gestational inquiry is suitable for the user for the current gestational phase; and
   evaluating the gestational inquiry to determine eligibility for subsequent gestational phases.

8. The system of claim 1, wherein determining the gestational eligibility of the gestational inquiry further comprises:
   determining that the gestational inquiry is suitable for the user; and
   initiating a limitation on the gestational inquiry.

9. The system of claim 1, wherein determining the gestational eligibility of the gestational inquiry further comprises:
   determining that the gestational inquiry is not suitable for the user;
   identifying suitable gestational inquiries related to the inquiry category; and
   recommending suitable gestational inquiries related to the inquiry category as a function of the user biological extraction and the user gestational phase.

10. The system of claim 1, wherein determining the gestational eligibility of the gestational inquiry further comprises:
    determining that the gestational inquiry is not suitable for a first gestational phase; and
    determining that the gestational inquiry is suitable for a second gestational phase wherein the second gestational phase occurs after the first gestational phase.

11. A method of physiologically informed gestational inquiries, the method comprising:
    calculating by a computing device, a gestational phase wherein calculating the gestational phase further comprises:
    receiving a gestational datum;
    classifying the gestational datum to a gestational phase; and
    generating a gestational phase label;
    receiving by the computing device, from a remote device operated by a user, a gestational inquiry;
    classifying by the computing device the gestational inquiry to an inquiry category;
    selecting by the computing device a gestational machine-learning model as a function of the inquiry category;
    generating by the computing device a gestational machine-learning model, wherein the gestational machine-learning model utilizes the gestational phase label and a user biological extraction as an input and outputs gestational eligibility labels; and
    determining by the computing device utilizing the gestational machine-learning model the gestational eligibility of the gestational inquiry.

12. The method of claim 11, wherein classifying the gestational datum to a gestational phase further comprises generating a gestational classification algorithm, wherein the gestational classification algorithm utilizes the gestational datum as an input and outputs a gestational phase label.

13. The method of claim 11, wherein receiving the gestational inquiry further comprises receiving at an image catching device located on the computing device a wireless transmission from the remote device containing a picture of the gestational inquiry.

14. The method of claim 11, wherein receiving the gestational inquiry further comprises:
    receiving from the remote device a description of the gestational inquiry; and
    separating the gestational inquiry from the description of the gestational inquiry.

15. The method of claim 11, wherein classifying the gestational inquiry to an inquiry category further comprises generating a category classification algorithm wherein the category classification algorithm utilizes the gestational inquiry as an input and outputs an inquiry category.

16. The method of claim 11, wherein generating the gestational machine-learning model further comprises:
    receiving gestational training data wherein gestational training data further comprises a plurality of combinations of gestational phase labels and biological extractions and correlated to gestational eligibility; and outputting a plurality of gestational eligibility labels for gestational inquiries related to the inquiry category.

17. The method of claim 11, wherein determining the gestational eligibility of the gestational inquiry further comprises:

determining the gestational inquiry is suitable for the user for the current gestational phase; and evaluating the gestational inquiry to determine eligibility for subsequent gestational phases.

18. The method of claim 11, wherein determining the gestational eligibility of the gestational inquiry further comprises:

determining the gestational inquiry is suitable for the user; and initiating a limitation on the gestational inquiry.

19. The method of claim 11, wherein determining the gestational eligibility of the gestational inquiry further comprises:

determining the gestational inquiry is not suitable for the user;

identifying suitable gestational inquiries related to the inquiry category; and recommending suitable gestational inquiries related to the inquiry category as a function of the user biological extraction and the user gestational phase.

20. The method of claim 11, wherein determining the gestational eligibility of the gestational inquiry further comprises:

determining the gestational inquiry is not suitable for a first gestational phase; and determining the gestational inquiry is suitable for a second gestational phase wherein the second gestational phase occurs after the first gestational phase.

* * * * *